United States Patent [19]

Miller, Jr. et al.

[11] Patent Number: 4,679,428
[45] Date of Patent: * Jul. 14, 1987

[54] INDEPENDENT ANALYSIS OF ANIONS AND CATIONS USING INDIRECT PHOTOMETRIC CHROMATOGRAPHY

[75] Inventors: Theodore E. Miller, Jr.; Ziad Iskandarani, both of Midland, Mich.

[73] Assignee: The Dow Chemical Company, Midland, Mich.

[*] Notice: The portion of the term of this patent subsequent to Feb. 4, 2003 has been disclaimed.

[21] Appl. No.: 822,188

[22] Filed: Jan. 24, 1986

Related U.S. Application Data

[63] Continuation of Ser. No. 682,032, Dec. 12, 1984, Pat. No. 4,567,753.

[51] Int. Cl.[4] .......................................... G01N 31/04
[52] U.S. Cl. .................................................. 73/61.1 C
[58] Field of Search ................ 73/61.1 C; 422/70; 436/161; 356/72

[56] References Cited

U.S. PATENT DOCUMENTS

| | | | |
|---|---|---|---|
| 3,918,906 | 11/1975 | Small et al. | 73/61.1 C X |
| 3,920,397 | 11/1975 | Small et al. | |
| 4,017,262 | 4/1977 | Small et al. | 73/61.1 C X |
| 4,265,634 | 5/1981 | Pohl | 73/61.1 C X |
| 4,367,041 | 1/1983 | Webb, Jr. et al. | 73/61.1 C X |
| 4,383,047 | 5/1983 | Stevens et al. | 521/28 |
| 4,414,842 | 11/1983 | Small et al. | 73/61.1 C |
| 4,455,084 | 6/1984 | Webb, Jr. et al. | 73/61.1 C X |

OTHER PUBLICATIONS

H. Small and T. E. Miller, *Anal. Chem.*, 54 (1982), 462–469, "Indirect Photometric Chromatography".
H. Small, T. S. Stevens & W. C. Bauman, *Anal. Chem.*, 47 (1975) 1801–1809, "Novel Ion Exchange Chromatographic Method Using Conductimetric Detection".
T. S. Stevens, J. C. Davis, & H. Small, *Anal. Chem.*, 53 (1981) 1488–1492, "Hollow Fiber Ion-Exchange Suppressor for Ion Chromatography".
P. R. Haddad & A. L. Heckenberg, *J. Chromatogr.*, 252 (1982) 177–184, "High Performance Liquid Chromatography of Inorganic and Organic Ions... Detection".
I. Molnar, H. H. Nauer & D. Wilk, *J. Chromatogr.*, 201 (1980) 225–240, "High Performance Liquid Chromatography of Ions".
N. E. Skelly, *Anal. Chem.*, 54 (1982) 712–715, "Separation of Inorganic and Organic Anions on Reversed-Phase... Columns".
B. Sachok, S. N. Deming and B. A. Bidlingmeyer, *Journal of Liquid Chromatography*, 5(3) (1982) 389–402, "Quantitation of Alkyl Sulfonates Using UV Detector... Chromatography".
M. Yamamoto, H. Yamamoto and Y. Yamamoto, *Anal. Chem.*, 56 (1984) 832–834, "Simultaneous Determination of Inorganic Anions and Cations by Ion... Eluent".
D. R. Jenke, *Anal. Chem.*, 56, No. 13 (1984) 2468–2470, "Standardization of Transparent Analyte Response in Indirect Photometric Chromatography".
R. C. Kong, B. Sachok and S. N. Deming, *Journal of Chromatography*, 199 (1980) 307–316, "Combined Effects of pH and Surface-Active-Ion Concentration in Reversed... Chromatography".

(List continued on next page.)

*Primary Examiner*—Stewart J. Levy
*Assistant Examiner*—Joseph W. Roskos
*Attorney, Agent, or Firm*—Burke M. Holldorson

[57] ABSTRACT

An improved technique and apparatus for the independent measurement of anions and cations in solution, wherein the sample ions are chromatographically displaced in a plurality of ion exchange columns by an eluting ion which is or is made light-absorbing and wherein the sample ions are detectable from decrements in absorbance of the eluting ions as revealed by photometric monitoring; and the sample ions, cations and anions, are further detected independently by means for monitoring eluting anion and cation absorbance differences calibrated according to characteristic absorbance ratios of the selected eluting ion species at a plurality of wavelengths.

6 Claims, 10 Drawing Figures

OTHER PUBLICATIONS

C. A. Pohl and E. L. Johnson, *Journal of Chromatographic Science*, 18 (1980) 442–452, "Ion Chromatography—The State-of-the-Art".

B. A. Bidlingmeyer, *Journal of Chromatographic Science*, 18 Oct. (1980) 525–537, "Separation of Ionic Compounds by Reversed-Phase Liquid Chromatography . . . Techniques".

E. Heftmann, *Chromatography*, Third Edition, "A Laboratory Handbook of Chromatographic and Electrophoretic Methods".

"Instruction Manual for Model 788 Dual Variable Wavelength Detector," dated Dec. 17, 1982, 3-7, 3-8, 7-2 through 7-12.

(240 nm)   V (mL)

(270 nm)   V (mL)

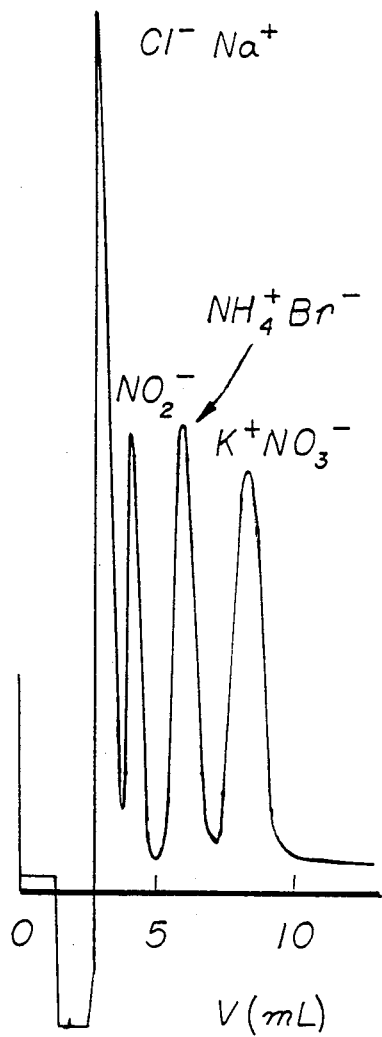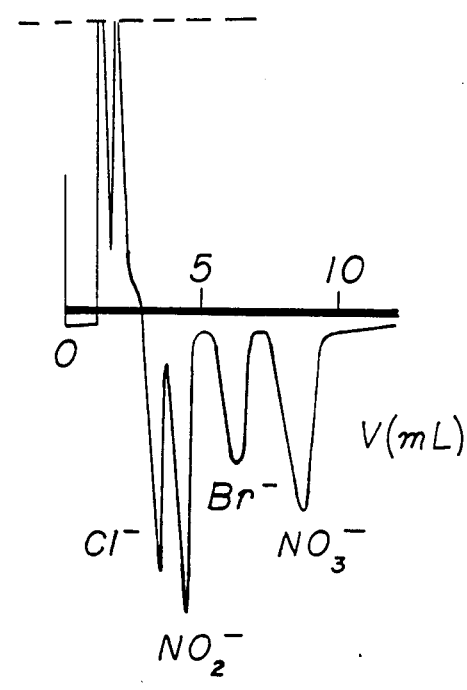
Fig. 9
Fig. 10

INDEPENDENT ANALYSIS OF ANIONS AND CATIONS USING INDIRECT PHOTOMETRIC CHROMATOGRAPHY

This is a continuation of application Ser. No. 682,032, filed Dec. 12, 1984, now U.S. Pat. No. 4,567,753.

FIELD OF THE INVENTION

This invention is in the field of ion exchange chromatography. It particularly concerns a method and apparatus for the independent analysis of coeluting sample anions and cations in a liquid effluent using Indirect Photometric Chromatographic (IPC) techniques.

BACKGROUND OF THE INVENTION

Liquid chromatography is used to separate the components of a sample substance by passing an eluent containing the sample through a column. The components of the sample in the eluent stream have different retention times within the column, and therefore exit the column in a particular sequence depending on the nature of the components of the sample and the nature of the column. The sequence of components is detected, for example, photometrically by measuring the intensity of light absorbed by the eluent stream.

Developments in liquid chromatography have led beyond component separation and analysis to ion separation and analysis. Ion exchange liquid chromatography is often complicated by limitations in the capability to detect the eluted sample ions in the column effluent. For example, many inorganic and organic ions are non light-absorbing and difficult to detect using conventional photometric detectors. Even though the separation of such "transparent" ions may be conveniently effected using ion exchange resin columns, the detection and measurement of these transparent ions by conventional photometric means is ineffective since they are optically indistinguishable from the transparent eluents commonly prescribed by the art. Hence, practices using photometers to detect ions in effluent have been effective only when the ions to be analyzed either contain chromophores or can generate chromophores through post-column reactions with appropriate reagents.

The problems of transparent ion detection are in part solved by the recent development of Indirect Photometric Chromatography (IPC). IPC has been described in detail in U.S. Pat. No. 4,414,842. IPC involves a method and apparatus for measuring ions in a sample undergoing chromatographic analysis wherein the ions of interest are transparent at the wavelengths monitored by the photometer. In the IPC method, these ions are first displaced from the ion exchange column in which they have been selectively adsorbed, by passing through the column, an eluent containing eluting ions which are or are made light absorbing. The displaced sample ions as they appear in the eluent are then detected in series and quantified by observing the decrements the ions cause in eluent absorbance, as revealed by photometric monitoring. For further details of IPC principles and techniques, see, "Indirect Photometric Chromatography", *Anal. Chem.*, 1982, 54, 462–469, written by Small and Miller. Both of the above references are incorporated herein.

A problem with the known IPC method arises when an attempt is made to carry out independent analysis of both anions and cations, both of which are transparent. Since such ions in the mobile or eluent phase both contribute to the absorbance of UV wavelengths, it has not heretofore been found possible to measure independently, the eluent absorbance due to the individual anions and the individual cations.

One attempt was made to detect and record anions and cations eluting simultaneously from a column; see Yamamoto, Yamamoto, Yamamoto, Matsushita, Baba and Ikushige, "Simultaneous Determination of Inorganic Anions and Cations by Ion Chromatography with Ethylenediaminetetraacetic Acid as Eluent" *Anal. Chem.*, 56, 832–834, (1984). This attempt was not successful in independently determining the anion and cation concentrations as they eluted. The scientists noted that, "The retention times observed for $Ca^{2+}$ and $Mg^{2+}$, injected as metal cations, and those injected as EDTA chelate anions were not significantly different." To overcome this problem, the scientists converted the $Mg^{2+}$ and $Ca^{2+}$ cations to chelate anions using the EDTA eluent, separated the anion species for detection, and detected the anions using conventional chromatographic methods. The scientists specifically noted that $Mg^{2+}$ and $Ca^{2+}$ could not be found except as corresponding anion peaks in the chromatogram.

Even though detection systems have been developed for differentiating among pure components of an eluent stream, e.g., see U.S. Pat. No. 4,367,041, no detection system presently exists which can distinguish between transparent anion and cation species having identical or nearly identical retention times.

The present invention has as its object to provide a method and apparatus using indirect photometric chromatography techniques to detect independently anion and cation species of a sample within a single chromatograph even when the species have identical or nearly identical retention times. The technique of the present invention displaces sample anions and cations with photometrically monitorable eluent anion and cation species. The present invention teaches the use of an eluent containing a salt with chromophoric anion and cation species each having a known characteristic ratio of absorbance at predetermined wavelengths, and the use of certain mathematical equations to develop, independently two chromatograms, one for anions, and one for cations.

Other objects, features and advantages of the present invention will become apparent upon reading the following detailed description and examples, when taken together with the drawing and appended claims.

SUMMARY OF THE INVENTION

The invention relates to an ion chromatography method for simultaneous and fully independent analysis of sample cations and anions, the method comprising:
(a) eluting a sample containing transparent cations and anions through an ion exchange chromatography column means comprising a cation ion exchange-performing stationary phase and an anion ion exchange-performing phase;
(b) using as the eluent an electrolyte solution of effective displacing ions consisting essentialy of a single salt of a photometrically detectable cation and anion having constant absorptivity ratios, relative to two wavelengths, distinctive of the cation and anion;
(c) monitoring the absorbance of the effluent of the chromatography column means at different wavelengths at which the cation and anion have said constant absorptivity ratios distinctive of each; and (d) quantitatively analyzing the sample independently for sample cations and sample anions.

The invention further relates to ion chromatography apparatus for simultaneous and fully independent quantitative analysis of sample cations and anions based on use of indirect photometric chromatography, the apparatus generally comprising a liquid chromatography pump means, a sample injection means, an ion exchange liquid chromatography column means, and a photometric detector means in series, the improvement which comprises:

(a) as the chromatography column means, a cation ion exchange-performing stationary phase and an anion ion exchange-performing stationary phase; and (b) as the photometric detector, a liquid chromatography flow-through detector capable of simultaneously and continuously detecting light absorbance at different wavelengths and providing electrical signals proportional to the detected absorbances at the different wavelengths.

The present invention provides a method and apparatus for independently detecting photometrically indetectable anions and cations of a sample, regardless of the concentration of the sample, by chromatographically displacing the anions and cations of the sample using indirect photometric chromatography techniques. It should be noted that the phrase "regardless of the concentration of the sample" refers to concentrations of sample within normal chromatographic limitations. Eluent anions and cations, once photometrically detected, reveal the anion and cation of the sample by detection of the decrements caused in effluent absorbance of the eluent anions and cations when subjected to photometric monitoring at two preselected wavelengths, $\lambda_1$ and $\lambda_2$.

This method and apparatus invention is predicated on the existence of characteristic absorption spectra for the components of a selected eluent. More specifically, this invention is based on the fact that for a set of wavelengths, an eluent containing a single salt will exhibit constant absorptivity ratios, each distinctive for the anion and cation of the eluent salt. Each constant ratio is referred to hereafter as the "inherent relative absorbance ratio."

The general formula used in accordance with the principles and teachings of the invention is:

$$A_d = RA_{\lambda 1} - A_{\lambda 2}$$

wherein $A_d$, $A_{\lambda 1}$, and $A_{\lambda 2}$ are absorbance signals, and R is the inherent relative absorbance ratio for either an eluent anion or an eluent cation depending on the ion being measured. More specifically, if sample cations are to be measured then R is computed using the general formula:

$$R = \frac{A^-_{\gamma 2}}{A^-_{\gamma 1}}$$

where $A_{\lambda 1}^-$, represents the absorbance value of the anion species of the eluent at a first wavelength and $A_{\lambda 2}^-$ represents the absorbance value of the anion species at a second wavelength. If sample anions are to be measured, then R is computed using the general formula:

$$R = \frac{A^+_{\gamma 2}}{A^+_{\gamma 1}}$$

For example, if the salt copper ortho-sulfobenzoate (Cu o-SB) is used in the eluent, the general formula is written as follows:

$$A_d = RA_{240} - A_{270}$$

wherein for sample anion detection $$R = \frac{A^+_{270}}{A^+_{240}} ;$$

and for sample cation detection:

$$R = \frac{A^-_{270}}{A^-_{240}}$$

with wavelength values given in nanometers. Solving for the factor R for sample anion detection using experimental data, R is about 0.45. i.e., $$0.45 = \frac{A^+_{270}}{A^+_{240}}$$

and for sample cation detection R is about 0.74, i.e., $$0.74 = \frac{A^-_{270}}{A^-_{240}}$$

These R values are determined simply by ratioing cation peaks using detected absorbance at 240 and 270 nm and anion peaks using detected absorbance at these wavelengths.

Further, when the absorbance difference signal ($A_d$) for eluent anions is zero, then $A_d$ for sample cations is determined by the equation:

$$A_d = (0.74)A_{240} - A_{270}.$$

Similarly, when the absorbance difference signal ($A_d$) for eluent cations is zero, then $A_d$ for eluent sample anions is determined by the equation:

$$A_d = (0.45)A_{240} - A_{270}.$$

A basic feature of the invention is in the use of eluent having light absorbing anion and cation species capable of chromatographically displacing anions and cations of the sample of interest.

The eluent must contain light-absorbing anions and cations which:

(1) selectively displace the sample anions and cations from the chromatographic columns or ion exchange media, and (2) reveal the sample anions and cations in the effluent.

The eluent which performs these two functions contains anions and cations which displace the transparent sample anions and cations from the column and enable the anions and cations of the sample to be detected in the column effluent as dips or troughs in the baseline absorbance of the anions and cations of the eluent.

The eluent must contain light-absorbing anions and cations which have UV or light absorption coefficients such that the anion will not completely mask the cation, nor vice versa. Also, the eluent must contain anions and cations of appropriate displacing power to elute the sample ions from the column in a reasonable amount of time, i.e., allowing resolution of peaks without excessive peak broadening. An ideal eluent should contain anions and cations which exhibit absorbances of at least 0.1 AU at $10^{-3}$ molar with a path length of 1 cm at 220 nm or above.

The eluent should contain a "monitor/displacing" salt which is soluble in water and preferably either aromatic, organic, inorganic, polyvalent or monovalent, or a combination of these characteristics. Even more importantly, the eluent should not contain a second salt which may form spurious peaks upon photometric detection.

The eluent should have a pH which does not affect chromatographic column packing nor destroy the ionic nature of the chromatographic column. More specifically, the eluent must not have a low pH, such as pH 1, wherein eluent hydrogen ions would begin to function as the displacing ions in place of the intended eluent ions. Similarly, the eluent must not have a high pH, e.g., pH 12, such that the eluent precipitates metal in the eluent or alternatively causes the hydroxide to act as a displacing ion. A pH of less than 7 is preferred for most silica-based ion exchange columns. Eluents with a pH in the range of pH 4 to pH 5 are effective and useful within the teachings and principles of the invention.

The apparatus of the invention involves a system for independently measuring anions and cations of a sample using indirect photometric chromatography, an eluent comprising a soluble salt solution having chromophoric anions and cations and having an inherent relative absorbance ratio for the anions of an eluent at selected first and second wavelengths and for the cations of the same eluent at the same first and second wavelengths. The invention further involves an anion exchange stationary phase, a cation exchange stationary phase and a detector connected in series. The invention includes means for forming a stream of eluent flowing through the anion exchange stationary phase and the cation exchange stationary phase to the detector. The invention involves means for introducing a sample of interest into the stream of eluent and flowing the sample and eluent through the anion exchange and cation exchange stationary phase means to produce an effluent. The detector is preferably a multiple wavelength detector with means for receiving the effluent from the ion exchange stationary phases and measuring the total absorbance of the anions and cations in the effluent at a first wavelength and a second wavelength. The apparatus invention also includes circuitry responsive to the detector with means for using the inherent relative absorbance ratios distinctive for the eluent anions and cations and the detected total absorbance values for the effluent at first and second wavelengths to determine separately sample anion and sample cation concentrations. The apparatus invention can further involve recording means for recording the individual responses corresponding to the anions and cations of the sample.

The particular circuitry of the instant invention consists of means for using the inherent relative absorbance ratio for each eluent ion to scale the detected total absorbance value of the effluent ions at a first wavelength to produce a scaled value and subtracting the detected total absorbance value of the effluent at a second wavelength from the scaled detected total absorbance value at the first wavelength to produce individual absorbance values for the eluent anion and cation, eliminating the effect of fluctuations in eluent anion and cation concentrations and subsequently revealing fluctuations in sample anion and cation concentrations.

TERMS

Throughout this specification terms particular to liquid chromatography and this invention will be used. The definitions of these terms follows:

"Transparent"—This term refers to the inability of lesser ability of an anion or cation of a sample of interest to absorb light at the selected wavelengths or be photometrically detected relative to the light absorbance property of an eluent.

"Eluent"—This term refers to the mixture of the specified salt in deionized LC quality water without sample, e.g., copper ortho-sulfobenzoate in LC quality water.

"Effluent"—This term refers to the aqueous mixture which results from passing eluent through the medium capable of performing the ion exchange.

"Wavelength"—This term refers to a wavelength or a wavelength band.

"Inherent relative absorbance ratio"—This expression denotes the quotient of optical absorbances at two different specified wavelengths for a single ionic species employed in the eluent. Since spectral features are generally independent of species concentration, this ratio remains constant as the concentration of an absorbing species varies.

"Ion exchange-performing stationary phase"—This term refers to a stationary phase for performing ion exchange liquid chromatographic separations which is an ion exchange material or which is or can be rendered an ion exchange performing material under the influence of a specified eluent.

BRIEF DESCRIPTION OF THE DRAWINGS

The invention may be explained with reference to the accompanying drawings in which:

FIGS. 2 through 10 are chromatograms made using the apparatus and following the procedures in the various examples below.

DESCRIPTION OF THE INVENTION

Figure 1:
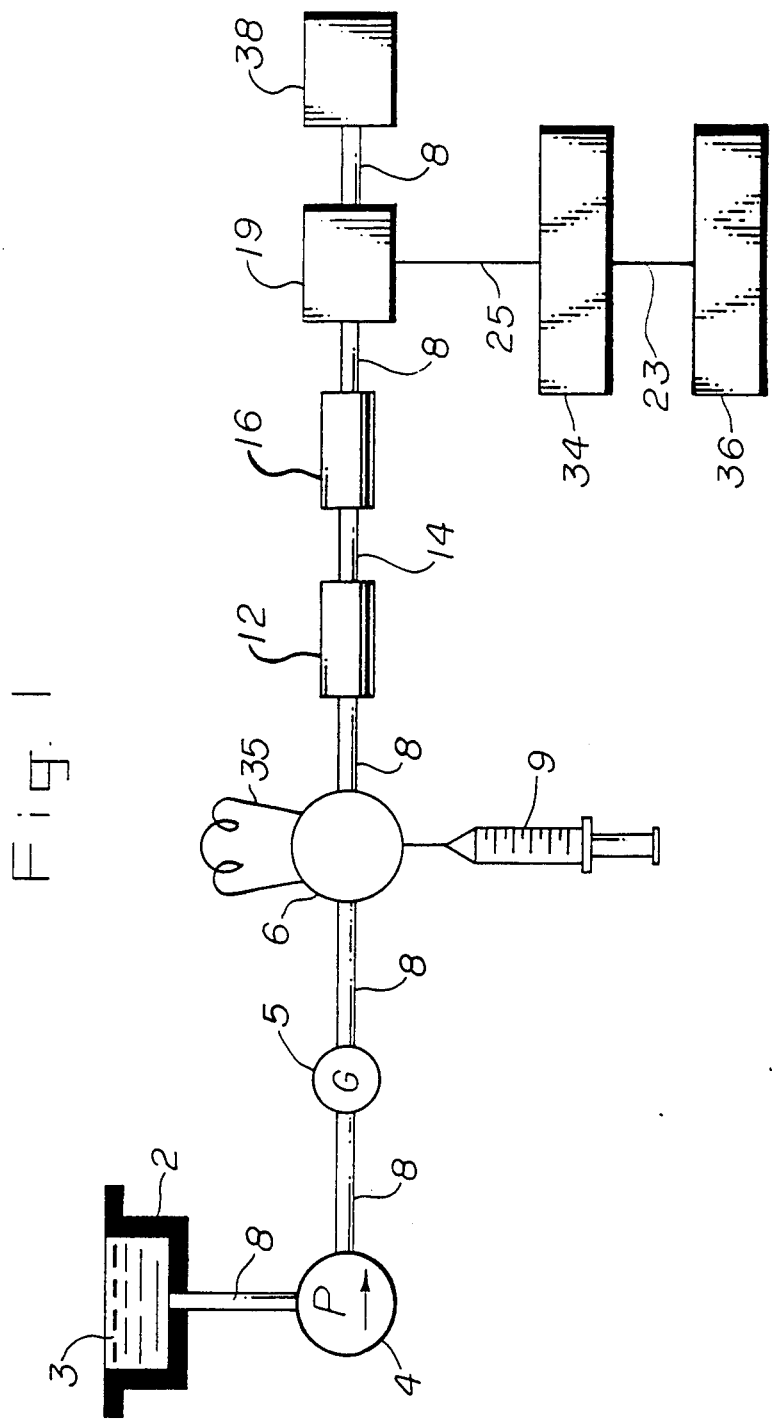
FIG. 1 is a diagram of apparatus according to the principles and teachings of the present invention.

Referring to FIG. 1, there is shown a typical diagram of an ion exchange chromatography system or apparatus which is desirably used in practicing the invention. The apparatus includes separating means such as two liquid chromatography columns 12 and 16 which are packed with media or stationary phase capable of performing ion exchange separations. Most chromatographic ion exchange media are in the pellicular or micro-particular form. Alternatively, the invention may employ a non-ion exchange chromatographic medium or stationary phase which is or can be rendered ion exchange-performing under the influence of the specified eluent. For example, a $C_{18}$ reverse phase LC column could be used as one of the preferred separating means; such as the work reported by Skelly, N. E. *Anal. Chem.*, 54, No. 4, 1982, pp. 712-715.

Columns 12 and 16 are connected to a photometric detector 19. Detector 19 is a flow-through UV photometer with micro-volume cell design for high performance liquid chromatography (HPLC) applications. Detector 19 is connected with waste vessel 38 for receiving the analyzed effluent.

Sample may be placed into the eluent stream flowing into column 12 using any suitable device but preferably using a syringe 9 to load an injection valve 6 having a sample loop 35. The injected sample is swept through column 12 and then column 16 with eluent 3 containing monitor/displacing light-absorbing anions and cations. Eluent 3 is drawn through tubing 8 from eluent reservoir 2 preferably using a chromatographic pump 4. The pressure of the eluent stream is preferably monitored by a pressure gauge 5. A first ion exchange occurs in column 12. Effluent from column 12 is passed through tubing 14 to column 16 wherein a second ion exchange appears. Effluent from column 16, containing resolved anions and cations is flowed to the photometric detector 19 through tubing 8. Tubing 8 preferably is conventional tubing with an 0.02 inch I.D. Tubing 14 is preferably a short length of 1/16 inch HPLC tubing. Photometric detector 19 is in electronic communication with circuitry 34 and recording means 36.

Additionally, pump 4 of this embodiment is a standard liquid chromatographic pump capable of operation with non-pulsing flow rates in the appropriate range. As an example, pump 4 could utilize a flow rate in the range of greater than 0.5 cc/min and less than 5 cc/min. The pump 4 is capable of providing pressure on the system within the range of 100-6000 psig.

The columns of this embodiment are preferably anion exchange and cation exchange columns connected in series as columns 12 and 16. The particular columns useful in this method and apparatus are columns with a total capacity in milliequivalents (meq) preferably in the range of $10^{-3}$ to 10 meq.

Silica columns are particularly useful in this invention. Other columns which can be used within the principles and teachings of this invention include surface sulfonated cation exchange resins and surface agglomerated latex anion exchangers with resin substrates.

These separating columns useful in this invention are preferably commercially available anion and cation exchange columns with low anion and cation exchange capacities. Preferably, the separating columns are strong anion and cation exchangers. As an example, a ZIPAZ® SAX or SCX duPont column, with pre-packed dimensions of 2.1 mm×500 mm is useful within the principles and teachings of this invention.

Detector 19 is preferably an ultraviolet light detector; however, another detector can be used within the scope of the invention provided the detector offers a variable parameter to selectively enhance the detectability of eluent components.

In the photometric detector 19, the absorbance of the light-absorbing eluent anions and cations is measured both at a first wavelength $\lambda_1$ and at a second wavelength $\lambda_2$. These measured absorbance values are then converted into signals which are passed by means 25 to circuitry 34 for mathematical manipulation. The circuitry 34 determines the absorbance difference values for cations and anions individually using the general formula:

$$A = RA_{\lambda_1} - A_{\lambda_2}$$

for measuring ions in the sample, wherein $A_{\lambda_1}$ is the total absorbance of the effluent at a first wavelength;

$A_{\lambda_2}$ is the total absorbance of the effluent at a second wavelength; and R is the known inherent absorbance ratio for a given eluent ion.

A computer may be used as the circuitry 34 to reveal the individual chromatograms or alternatively store and process the chromatographic patterns into sample ion data without recording the actual chromatograms. Similarly, the circuitry 34 can be used for sample cation chromatograms.

The data resulting from these computations then can be transmitted over means 23 to recording means 36, such as a strip chart recorder with dual tracing capabilities, or alternatively to two recorders connected in parallel, each of which is capable of recording the respective absorbance information. Recording means 36 can consist of any form of storage device, such as a computer memory, chart paper or digital readouts.

The concentrations of sample anion and cation can be determined independently and simultaneously using the above described apparatus.

The method and apparatus of the present invention require a specified eluent to achieve the objects of the invention. The preferred characteristics of the eluent are described in the subsequent paragraphs.

An ideal eluent is one which can exhibit UV absorbance spectra with a maximum absorbance wavelength for anion absorbance and a minimum absorbance wavelength for cation absorbance. Alternatively, an ideal eluent is one which can exhibit UV absorbance spectra with a minimum absorbance wavelength for anion absorbance and a maximum absorbance wavelength for cation absorbance. The eluent should have an absorbance within a range of 0.1 to 3.0 AU at the selected wavelengths. In the preferred embodiment, the eluent should exhibit an absorbance within the range of 0.5 to 1.5 AU at suitable wavelengths.

The eluent should also have UV absorbing qualities capable of revealing low concentrations of transparent anions and cations during Indirect Photometric Chromatography (IPC). An ideal eluent should contain less than about $5 \times 10^{-2}$ molar of displacing anions and cations for the purpose of sensitive detection using the IPC method of analysis. A preferred molarity for the eluent is within the range of $5 \times 10^{-5}$ to $5 \times 10^{-2}$ molar, ideally between $5 \times 10^{-5}$ to $5 \times 10^{-3}$.

An ideal eluent has an eluting power such that it produces a sample ion k' within the scope of 0.5 to 50 at eluent concentrations ranging from $10^{-5}$ to $10^{-1}$ molar. A preferred eluent develops k' within the range of 1 to 20 at concentrations ranging from $10^{-5}$ to $10^{-2}$ molar. (k' refers to the expression:

$$(V_E - V)/V,$$

where $V_E$ equals sample ion elution volume and V is the void volume).

In a preferred embodiment, the eluent of the instant invention should be capable of being easily prepared from analytical grade reagents and capable of being prepared so that no secondary salt is present. One such preferred eluent, which exhibits two different absorption spectra for its anion and cation, is easily prepared from analytical reagent grade ortho-sulfobenzoic acid cyclic anhydride (o-SBA) and copper (II) hydroxide. This preferred eluent comprises copper ortho-sulfobenzoate having the structural formula:

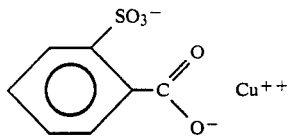

A particularly effective eluent salt is one which is multivalent, aromatic, and with a high molecular weight. Effective eluents are prepared by dissolving weighed amounts of the salts in deionized LC quality water. As an example, copper ortho-sulfobenzoate can be prepared by dissolving known weights of o-SBA cyclic anhydride and $Cu(OH)_2$ in deionized water to give the required equi-normal concentrations.

Other eluents which meet these criteria include benzyl-trimethylammonium nitrate. Benzyl-trimethylammonium eluent cation, ($BTA^+$), exhibits an inherent relative absorbance ratio of about 5.13 for sample anion detection, i.e., $$R = \frac{A^+_{260}}{A^+_{230}} = 5.13$$

For sample cation detection, nitrate eluent anion, ($NO_3^-$), exhibits an inherent relative absorbance ratio of about 0.025, i.e., $$R = \frac{A^-_{260}}{A^-_{230}} = 0.025$$

It should be noted that the monovalency of both eluent species tends to reduce the sensitivity of detection compared to that of divalent $Cu^{++}o\text{-}SB^{--}$ which can be employed at lower eluent concentrations. Also $BTA^+$ exhibits a disproportionately strong sample eluting power relative to nitrate.

Another eluent is copper nitrate ($Cu^{+2}(NO_3^-)_2$). $Cu^{+2}$ exhibits an inherent relative absorbance ratio of 0.248 for sample anion detection, i.e., $$R = \frac{A^+_{263}}{A^+_{233}} = 0.248$$

For sample cation detection, nitrate, the eluent anion, exhibits an inherent relative absorbance ratio of 0.031 at these same wavelengths, i.e., $$R = \frac{A^-_{263}}{A^-_{233}} = 0.031$$

For this eluent, the equi-normal nitrate is very weak as a displacing ion relative to divalent copper and the sample anions are highly retained relative to sample cations.

Additional eluents that have been considered include copper phthalate, copper trimesate, copper iodide, and pyridinium (aromatic cation) salts. In each of these cases, spectral data shows that one ion of the pair would exhibit an extreme degree of optical absorbance relative to the other, masking the counterion's absorbance at every wavelength.

Benzyltrimethyl ammonium iodide ($BTA^+I^-$) would be expected to be suitable using 250 and 270 nm detection wavelengths but monovalency would again be expected to limit sensitivity relative to divalent Cuo-SB.

The following examples further detail the principles and teachings of the present invention. Additional objectives, aspects and advantages of the invention will be apparent from the following examples.

EXAMPLE 1

In this example, the apparatus includes an eluent reservoir, a Laboratory Data Control (LDC) Constametric I pump, a Rheodyne Model 7010 injection valve, a duPont ZIPAX® SAX column, and a duPont ZIPAX® SCX column both prepacked and 2.1 mm×500 mm, a Micromeritics Model 788 dual variable wavelength detector and a Linear Model 585 dual channel recorder.

The preferred eluent is prepared from analytical reagent grade ortho-sulfobenzoic acid cyclic anhydride (o-SBA), and copper hydroxide to form a $5 \times 10^{-4}$ molar mobile phase copper ortho-sulfobenzoate eluent. More particularly, the $5 \times 10^{-4}$ molar copper ortho-sulfobenzoate eluent is prepared by dissolving 92.1 milligrams of ortho-sulfobenzoic acid cyclic anhydride (FW 184.17) and 48.8 milligrams of copper (II) hydroxide (FW 97.54) into each liter of water (LC quality water). The solution is stirred until all particles are dissolved and the pH of the eluent is measured to be in the range of pH 4 to pH 6.

Eluent is placed in the reservoir and the LDC Constametric pump draws eluent from the reservoir and pumps it to a duPont ZIPAX® SAX column at a flow rate of about 1.0 milliliter per minute with an inlet pressure of 2200 psi for this first of the two columns in series. A 20 microliter sample aliquot containing $10^{-3}$ molar of $NH_4Cl$ and $10^{-3}$ molar $K_2SO_4$ is injected into the stream of eluent between the pump and the first column using the Rheodyne Model 7010 sample injector valve. Anion exchange occurs in the first column and effluent from the first column then proceeds into a second ZIPAX® SCX column. The inlet pressure for the second column is approximately 1100 psi and approaches 0 psig between the inlet and outlet of this ZIPAX® SCX column. Effluent from the SCX column is flowed into a Micromeritics Model 788 dual variable wavelength detector. In the detector, the effluent from the second column enters a cell having windows disposed at opposite ends. Light is passed from a light source through the first set of windows, the effluent, and a second set of windows to a variable angle concave grating which separates the light waves into at least two distinct wavelengths. The light beams at these wavelengths are then detected. In this example, UV detection is performed at two wavelengths, 270 and 240 nm. The instrument then passes the detected effluent absorbance values to circuitry or alternatively other means for mathematically manipulating the data relative to the general formula $A_d = RA_{\lambda 1} - A_{\lambda 2}$. The manipulated data is subsequently communicated to a Linear Model 585 multichannel recorder.

An interesting, useful feature of the invention is that sample anions and cations exhibit two different but constant ratios of peak heights or areas at 270 nm relative to 240 nm. These known inherent relative absorbance ratios are values equivalent to the ratios of the inherent molar absorptivities of $Cu^{++}$ and $o\text{-}SB^{--}$ at the two wavelengths, 270 nm and 240 nm, in accordance with the principles of IPC. This feature allows immediate identification of peaks as anion or cation.

Figure 2:
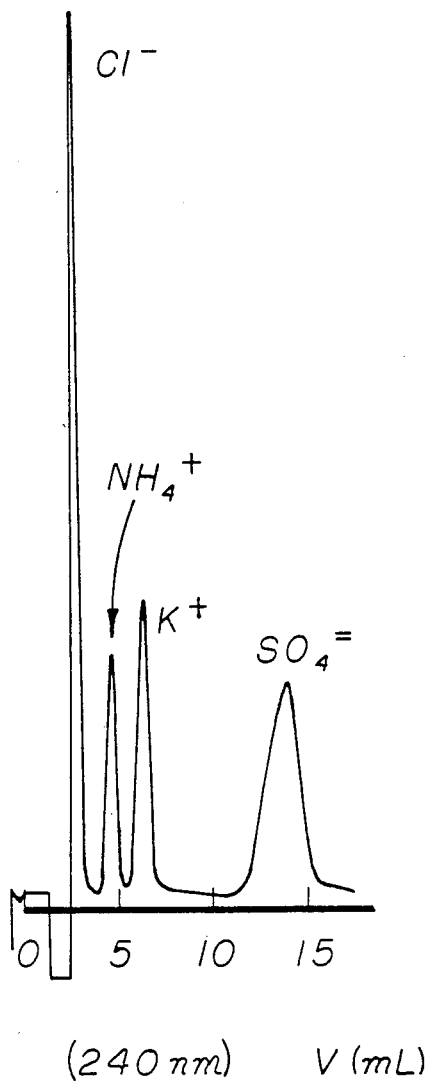
Figure 3:
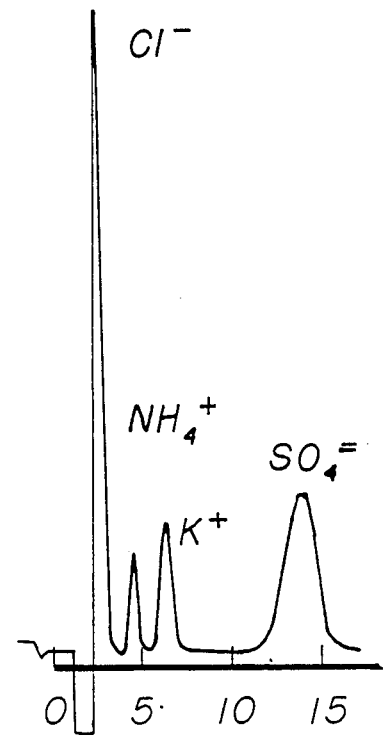
Figure 4:
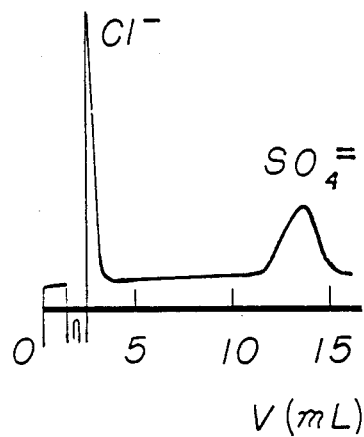
Figure 5:
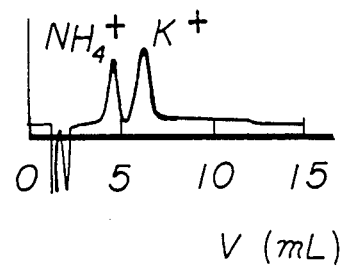
Figure 7:
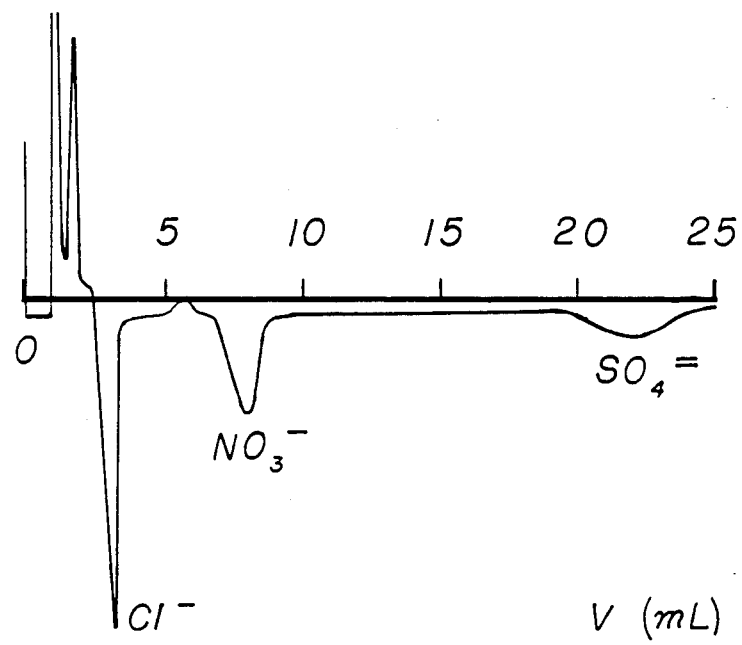

At wavelengths 270 nm and 240 nm $o\text{-}SB^{--}$ exhibits a constant ratio of 0.74 while $Cu^{++}$ exhibits a constant ratio of 0.45. FIGS. 2–5 are the chromatograms resulting from using Cuo-SB in accordance with the parameters of Example 1. FIG. 2 is the chromatogram measured at 240 nm. FIG. 3 is the chromatogram measured at 270 nm. FIG. 4 is a chromatogram representing the detection of anions alone, i.e., $A_d = (0.45)A_{240} - A_{270}$. FIG. 5 is a chromatogram representing the detection of cations alone, wherein $A_d = (0.74)A_{240} - A_{270}$. For purposes of illustration, the FIG. 4 chromatogram is inverted. A consequence of the method is to invert the anion chromatograms as seen in FIGS. 7 and 10.

EXAMPLE 2

Figure 6:
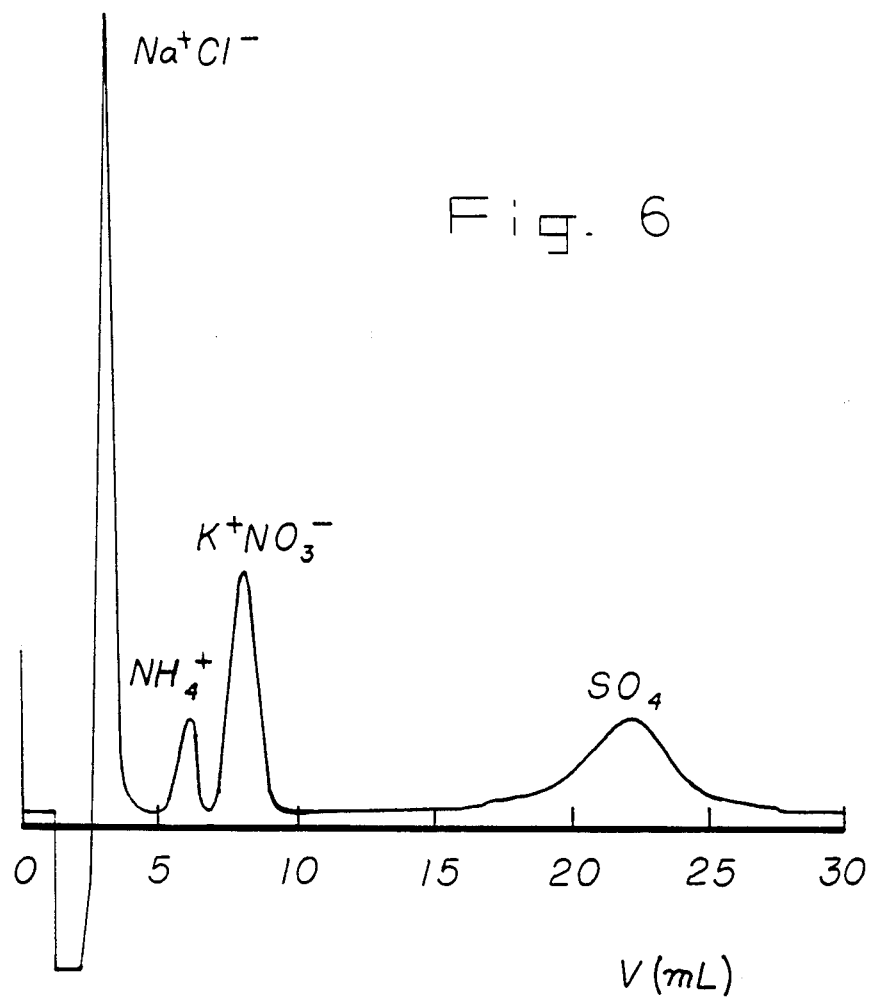
Figure 8:
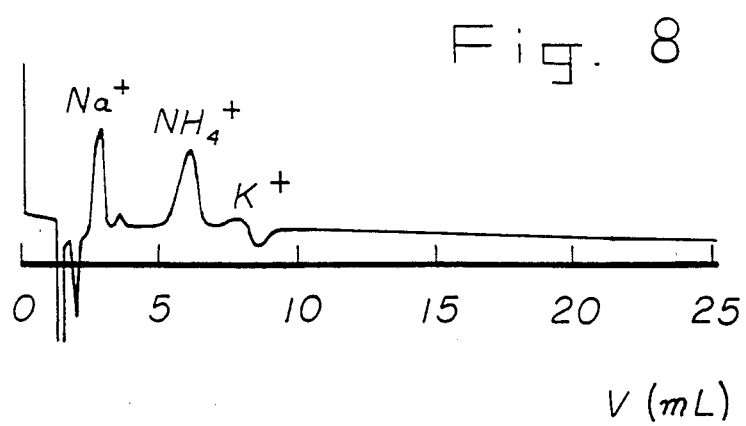

This example illustrates the separation of anions and cations of a synthetic acid rain sample ($Na^+$, $NH_4^+$, $K^+$, $Cl^-$, $NO_3^-$, $SO_4^{--}$) using an eluent of $2.5 \times 10^{-4}$M Cuo-SB. FIG. 6 is a chromatogram of two completely resolved peaks ($NH_4^+$, $SO_4^{--}$) and the coelution of the other compounds as only two peaks ($Na^+$, $Cl^-$ and $K^+$, $NO_3^-$) which are nonetheless also completely revolved by the method of the invention. Employing the method taught by this invention, the independent analysis of anions and cations results in the chromatograms of FIGS. 7 and 8, respectively. FIG. 8 shows the interference of a negative peak with the $K^+$ peak. This interference is due to the absorbance of $NO_3^-$ ion at 240 nm which results in an interference with the detection mode of IPC resulting in a peak height ratio different from 0.74. This kind of chromatographic result will occur for those few sample ions that absorb at either 270 nm or 240 nm wavelengths of detection. This peak interference difficulty is easily overcome if the sample ion is transparent at one of the detection wavelengths, as is the case with nitrite ($NO_2^-$) and nitrate ($NO_3^-$). Example 3, following, illustrates how this is accomplished.

EXAMPLE 3

This example shows the applicability of the present invention to the chromatographic analysis of anions and cations in complex mixtures including nitrite and nitrate. Using the apparatus of Example 1, a 20 μl $10^{-3}$M sample containing $Na^+$, $NH_4^+$, $K^+$, $Cl^-$, $NO_2^-$, $Br^-$, and $NO_3^-$ is injected into the system using a mobile phase of $2.5 \times 10^{-4}$M copper ortho-sulfobenzoate. FIG. 9 shows the combined chromatogram observed at 270 nm, where both nitrite and nitrate are transparent. FIG. 10 illustrates the anion chromatogram developed using the method of the invention. The potassium ($K^+$) peak, coeluting with nitrate, is quantified from the difference in peak magnitudes between the combined peak (FIG. 9) and the nitrate peak alone (FIG. 10).

What is claimed is:

1. An ion chromatography method for simultaneous and fully independent analysis of sample cations and anions, the method comprising:
   (a) eluting a sample containing transparent cations and anions through an ion exchange chromatography column means comprising a cation ion exchange-performing stationary phase and an anion ion exchange-performing phase,
   (b) using as the eluent an electrolyte solution of effective displacing ions consisting essentially of a single salt of a photometrically detectable cation and anion having constant absorptivity ratios, relative to two wavelengths, distinctive of the cation and anion,
   (c) monitoring the absorbance of the effluent of the chromatography column means at different wavelengths at which the cation and anion have said constant absorptivity ratios distinctive of each, and
   (d) quantitatively analyzing the sample independently for sample cations and sample anions.

2. The ion chromatogrphy method of claim 1 including the step of recording individual chromatograms of the sample cations and anions.

3. The ion chromatography method of claim 1 or 2 wherein step (a) comprises using stationary phases which are ion exchange materials.

4. Ion chromatography apparatus for simultaneous and fully independent quantitative analysis of sample cations and anions based on use of indirect photometric chromatography, the apparatus generally comprising a liquid chromatography pump means, a sample injection means, an exchange liquid chromatography column means, and a photometric detector means in series, the improvement which comprises:
   (a) as the chromatography column means, a cation ion exchange-performing stationary phase and an anion ion exchange-performing stationary phase, and
   (b) as the photometric detector, a liquid chromatography flow-through detector capable of simultaneously and continuously detecting light absorbance at different wavelengths and providing electrical signals proportional to the detected absorbances at the different wavelengths.

5. The ion chromatography apparatus of claim 4 which includes means to develop and record independent chromatograms of the sample cations and anions.

6. The ion chromatography apparatus of claim 4 or 5 wherein the stationary phases are ion exchange materials.

* * * * *

UNITED STATES PATENT AND TRADEMARK OFFICE
CERTIFICATE OF CORRECTION

PATENT NO. : 4,679,428
DATED : Jul. 14, 1987
INVENTOR(S) : Theodore E. Miller, Jr.; Ziad Iskandarani It is certified that error appears in the above—identified patent and that said Letters Patent is hereby corrected as shown below:

Col. 6, line 20, delete "of" and insert --or--.
Col. 7, Line 54, delete "ZIPAZ" and insert --ZIPAX--.
Col. 8, line 56, delete "scope" and insert --range--.
Col. 9, line 44, delete "SB$^{--}$" and insert --SB$^=$--.
Col. 11, lines 8 and 12, each occurrence, delete "SB$^{--}$" and insert --SB$^=$--;
 lines 29 and 31, each occurrence, delete "SO$_4^{--}$" and insert --SO$_4^=$--;
 line 34, delete "revolved" and insert --resolved--.
Col. 12, Claim 2, line 28, delete "chromatogrphy" and insert --chromatography--.

Cover Page, after "Attorney, Agent, or Firm" correct spelling of "Holldorson" to --Halldorson--.

Signed and Sealed this

First Day of March, 1988

Attest:

DONALD J. QUIGG

*Attesting Officer*     *Commissioner of Patents and Trademarks*